United States Patent
Hayashi et al.

(10) Patent No.: US 7,307,167 B2
(45) Date of Patent: *Dec. 11, 2007

(54) PRODUCTION METHOD OF 2,6-DIHALOPURINE

(75) Inventors: Taketo Hayashi, Osaka (JP); Hiroharu Kumazawa, Osaka (JP); Takehiko Kawakami, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 492 days.

This patent is subject to a terminal disclaimer.

(21) Appl. No.: 10/509,802

(22) PCT Filed: Apr. 3, 2003

(86) PCT No.: PCT/JP03/04259

§ 371 (c)(1),
(2), (4) Date: Sep. 29, 2004

(87) PCT Pub. No.: WO03/084958

PCT Pub. Date: Oct. 16, 2003

(65) Prior Publication Data
US 2005/0131229 A1 Jun. 16, 2005

(30) Foreign Application Priority Data
Apr. 4, 2002 (JP) ............................. 2002-102456

(51) Int. Cl.
*C07D 473/40* (2006.01)
*C07B 39/00* (2006.01)

(52) U.S. Cl. ....................................... 544/264
(58) Field of Classification Search ............. None
See application file for complete search history.

(56) References Cited

U.S. PATENT DOCUMENTS

| 2,844,576 A | 7/1958 | Goldman et al. |
| 3,314,938 A | 4/1967 | Kawashima |
| 6,936,713 B2 * | 8/2005 | Masai et al. ............ 544/264 |

FOREIGN PATENT DOCUMENTS

| EP | 0 543 095 A | 5/1993 |
| EP | 0 543 095 A2 | 5/1993 |
| EP | 0 684 243 A | 11/1995 |
| EP | 0 684 243 A1 | 11/1995 |
| EP | 1 172 365 A | 1/2002 |
| EP | 1 172 365 A1 | 1/2002 |
| JP | 45-11508 | 4/1970 |
| WO | WO-93/15075 A | 8/1993 |
| WO | WO-93/15075 A1 | 8/1993 |
| WO | WO-02/081472 A | 10/2002 |
| WO | WO-02/081472 A1 | 10/2002 |

OTHER PUBLICATIONS

Francom and Morris J. Robins J. Org. Chem.; 2003; 68(2) pp. 666-669.*
Graynskwonsschultzpg: "Combinatorial synthesis of 2,9-substituted purines" Tetrahedron Letters, Elsevier Science Publishers, Amsterdam, NL, vol. 38, No. 7, 1997, pp. 1161-1164.
Elion et al., J. of American Chem. Soc., vol. 78, pp. 3508-3510, (1956).
Dhanda et al., J. Chem. Soc., Perkin Trans. 1, pp. 3469-3475, (1999).
Harnden et al., J. Chem. Soc., Perkin Trans. 1, pp. 2207-2213, (1989).
Montgomery et al., J. of American Chem. Soc., vol. 80, pp. 404-408, (1958).
Robins et al., J. Org. Chem., vol. 19, pp. 930-933, (1954).
Gray et al., Tetrahedron Letters, vol. 38, No. 7, pp. 1161-1164, (1997).

* cited by examiner

Primary Examiner—Mark L. Berch
(74) Attorney, Agent, or Firm—Birch, Stewart, Kolasch & Birch, LLP

(57) ABSTRACT

By reacting the compound of the formula [Ia] or [Ib] with halosilane compound and an agent for diazo reaction, 2,6-dihalopurine of the formula [II] can be produced conveniently in a high yield and can be easily isolated, wherein each symbol is as defined in the specification

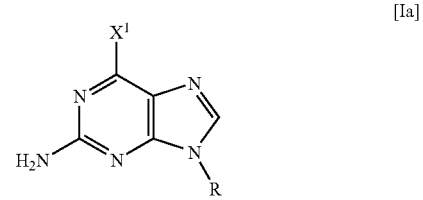

[Ia]

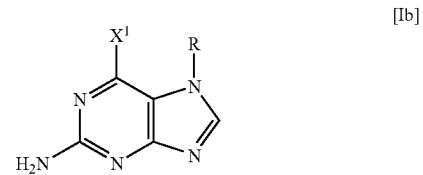

[Ib]

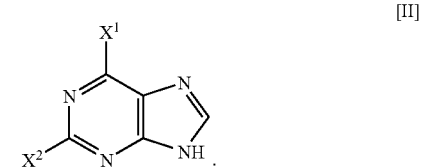

[II]

6 Claims, No Drawings

PRODUCTION METHOD OF 2,6-DIHALOPURINE

TECHNICAL FIELD

The present invention relates to a production method of 2,6-dihalopurine. More particularly, the present invention relates to a production method of 2,6-dihalopurine, which is useful as a starting material for a nucleoside analog and the like useful as a pharmaceutical product.

BACKGROUND ART

There are various production methods of 2,6-dihalopurine of the formula

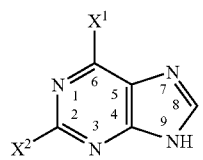

wherein $X^1$ and $X^2$ are the same or different and each is halogen atom. Known methods include, for example, (A) a method comprising chlorination of xanthine with pyrophosphoryl chloride (Journal of American Chemical Society, 78, 3508-10 (1956)), (B) a method comprising chlorination of N-oxide of hipoxanthine or 6-chloropurine with phosphorus oxychloride (JP-B-45-11508, U.S. Pat. No. 3,314,938), (C) a production method comprising 4 steps using barbituric acid derivative as a starting material (Journal of Organic Chemistry, 19, 930 (1954), Journal of American Chemical Society, 80, 404-8 (1958)), (D) a production method comprising cyclization of 2,4-dichloro-5,6-diaminopyrimidine (U.S. Pat. No. 2,844,576) and the like.

However, the aforementioned method (A) is associated with defects in that it requires preparation of pyrophosphoryl chloride as a chlorinating agent from phosphorus oxychloride by a complicated method, as well as a high reaction temperature of 165° C., the use of a corrosion resistant reaction container for the reaction and a long reaction time of about 19 hours. The aforementioned methods (A)-(D) are all defective in that they require long steps and complicated manipulations.

In addition, use of a method using a starting material, wherein the 9-position of the purine ring is alkylated, has been considered, and the following reaction was reported in, for example, J. Chem. Soc., Perkin Trans. 1, 1999, 3469-3475

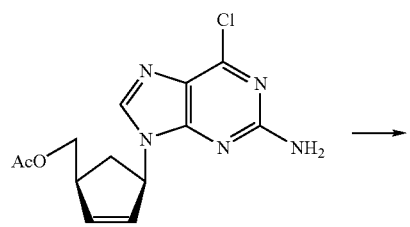

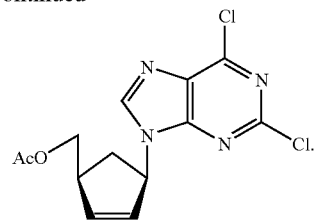

In this reaction, chlorotrimethylsilane and isoamyl nitrite were used in dichloromethane to give dichloropurine derivative, wherein the 9-position of the purine ring was alkylated, in a yield of 61%.

Furthermore, J. Chem. Soc., Perkin Trans. 1, 1989, 2207-2213 reports the following reaction

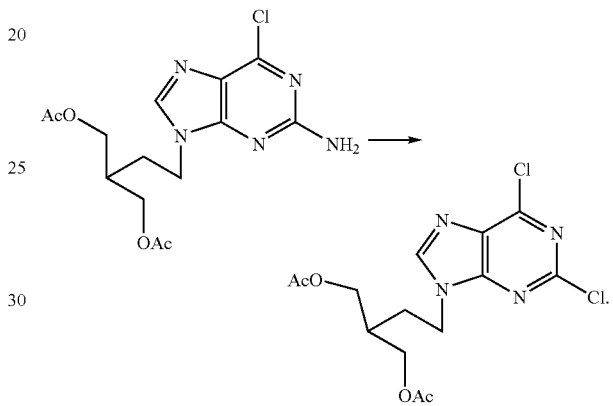

In this reaction, isoamyl nitrite was used in carbon tetrachloride to give dichloropurine derivative, wherein the 9-position of the purine ring was alkylated, in a low yield of 40%. To obtain the objective 2,6-dihalopurine, wherein the 9-position is unsubstituted, the alkyl group at the 9-position needs to be removed. However, there is no known method for this end, and conversion to 2,6-dihalopurine, wherein the 9-position is unsubstituted, is difficult. Thus, this method is not a preferable one.

In view of the above, the development of a convenient production method to afford the objective 2,6-dihalopurine in a high yield is desired, which allows easy isolation thereof.

It is therefore an object of the present invention to provide a method for conveniently producing the objective 2,6-dihalopurine in a high yield, which allows easy isolation thereof.

DISCLOSURE OF THE INVENTION

As a result of the intensive studies in an attempt to achieve the above-mentioned object, it has been found that, by reacting a compound of the formula [Ia] or [Ib]

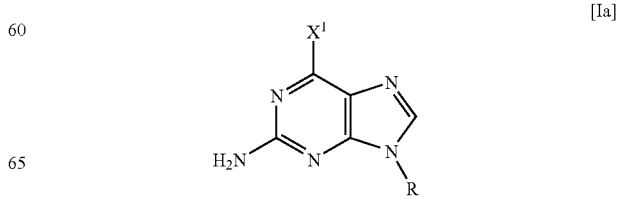

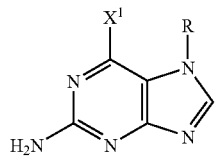

[Ib]

wherein X¹ is a halogen atom and R is a hydrogen atom or acyl group (hereinafter both to be abbreviated as compound [I] unless particularly specified) with halosilane compound and an agent for diazo reaction, 2,6-dihalopurine of the formula [II]

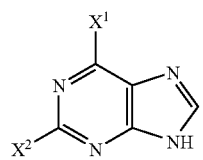

[II]

wherein X¹ and X² are the same or different and each is a halogen atom (hereinafter to be abbreviated as 2,6-dihalopurine) can be produced conveniently in a high yield, and that the objective product can be isolated easily.

Accordingly, the present invention provides the following.

(1) A production method of 2,6-dihalopurine, which comprises reacting compound [I] with a halosilane compound and an agent for diazo reaction.
(2) The production method of the above-mentioned (1), wherein the agent for diazo reaction is a nitrite ester.
(3) The production method of the above-mentioned (2), wherein the nitrite ester is isoamyl nitrite.
(4) The production method of the above-mentioned (1), wherein the reaction is carried out in the presence of a quarternary ammonium salt.
(5) The production method of the above-mentioned (4), wherein the quarternary ammonium salt is tetraethylammonium chloride or benzyltriethylammonium chloride.
(6) The production method of the above-mentioned (1), wherein R is an acyl group.
(7) The production method of the above-mentioned (6), wherein the acyl group for R is acetyl group.
(8) The production method of the above-mentioned (1), wherein the halosilane compound is chlorotrimethylsilane or dichlorodimethylsilane.
(9) The production method of the above-mentioned (1), wherein the halosilane compound is bromotrimethylsilane.
(10) The production method of the above-mentioned (1), wherein, after introducing an acyl group into the 9-position or the 7-position of compound [I], wherein R is a hydrogen atom, the obtained compound [I], wherein R is acyl group, is reacted with halosilane compound and the agent for diazo reaction.

DETAILED DESCRIPTION OF THE INVENTION

The 2,6-dihalopurine of the present invention encompasses tautomer.

The "acyl group" for R is a group represented by —C(=O)—R' wherein R' means, for example, a hydrocarbon group. The hydrocarbon group includes linear, branched chain or cyclic ones, which may be aliphatic or aromatic. Preferable acyl group includes alkylcarbonyl group having 2 to 6 carbon atoms (e.g., acetyl group, propionyl group, butanoyl group and the like), benzoyl group and the like. From the aspect of improvement in reactivity and economical aspect, acetyl group is particularly preferable. Since the acetyl group can be characteristically released easily by hydrolysis, compound [I], wherein R is acetyl group, can be easily converted to 2,6-dihalopurine.

The "halogen atom" for X¹ and X² is fluorine atom, chlorine atom, bromine atom or iodine atom, and X¹ and X² may be the same or different halogen atom.

The present invention is explained in detail in the following.

By a method comprising step for reacting compound [I] with halosilane compound and an agent for diazo reaction, 2,6-dihalopurine can be produced conveniently in a high yield, and the obtained 2,6-dihalopurine can be easily isolated. The R in compound [I] is preferably an acyl group, particularly preferably an acetyl group from the reactivity and releasability. In addition, this reaction in the presence of a phase transfer catalyst preferably accelerates the reaction rate. As the phase transfer catalyst in the present invention, for example, quarternary ammonium salt, crown ether (e.g., 12-crown-4, 15-crown-5, 18-crown-6 etc.), alkyl sulfate (e.g., sodium octylsulfate etc.), alkyl sulfonate (e.g., sodium octylsulfonate etc.) and the like can be included, with preference given to quarternary ammonium salt. The amount of the phase transfer catalyst to be used is a 0.005-0.2 molar amount, preferably 0.01-0.1 molar amount, per 1 mol of compound [I].

The "quarternary ammonium salt" in the present invention is not particularly limited, and, for example, tetraethylammonium chloride, benzyltriethylammonium chloride, trioctylmethylammonium chloride, benzyltrimethylammonium chloride and the like can be used, with preference given to tetraethylammonium chloride and benzyltriethylammonium chloride. When a quarternary ammonium salt is used, the use of a catalyst amount of, for example, 0.01-1 mol, preferably 0.05-0.1 mol, per 1 mol of compound [I] is sufficient.

In the halosilane compound to be used in the present invention, at least one halogen atom is bonded to silicon atom, or alkyl group may be bonded besides the halogen atom. Examples thereof include trialkylhalosilane, dialkyldihalosilane, monoalkyltrihalosilane and tetrahalosilane. The alkyl group here is a linear or branched chain alkyl group having 1 to 4, preferably 1 or 2, carbon atoms, such as methyl, ethyl, propyl, isopropyl, butyl, isobutyl, sec-butyl, tert-butyl and the like. The halogen atom here includes fluorine atom, chlorine atom, bromine atom and iodine atom.

Specific examples of the halosilane compound include chlorotrimethylsilane, dichlorodimethylsilane, trichloromethylsilane, tetrachlorosilane, bromotrimethylsilane and the like. Preferred are chlorotrimethylsilane, dichlorodimethylsilane and bromotrimethylsilane, and particularly preferred are chlorotrimethylsilane and dichlorodimethylsilane. The halosilane compound can be also used as a reaction solvent. The amount of use thereof is 1.5-30 mol, preferably 8-20 mol, per 1 mol of compound [I]. It is needless to say, when an organic solvent other than halosilane compound is used as a reaction solvent, the amount of halosilane compound to be used can be reduced from the above-mentioned range. The amount of halosilane compound to be used is 1-10 mol, preferably 1.5-6 mol, per 1 mol of compound [I].

As the agent for diazo reaction in the present invention, for example, nitrite ester, nitrosyl chloride, nitrosyl sulfate, nitrogen oxide, nitrite salt (e.g., sodium nitrite, potassium nitrite and the like) and the like can be used, with preference given to nitrite ester. As the nitrite ester, for example, $C_{1-5}$ alkyl nitrite (e.g., methyl nitrite, ethyl nitrite, propyl nitrite, isobutyl nitrite, tert-butyl nitrite, isoamyl nitrite and the like) and the like. Of these, isoamyl nitrite is preferable. The amount of the agent for diazo reaction to be used is 1-3 mol, preferably 1.1-1.5 mol, per 1 mol of compound [I].

The reaction of the present invention can be carried out in an organic solvent, and the organic solvent to be used is not particularly limited. From the aspects of reaction rate and suppression of by-product, hydrocarbon solvents such as hexane, heptane and the like, halogenated solvents such as monochlorobenzene, dichlorobenzene and the like, and tetrahydrofuran are preferable. Of these, the hydrocarbon solvents such as hexane, heptane and the like, or halogenated solvents such as monochlorobenzene, dichlorobenzene and the like are more preferable. The amount of the organic solvent to be used is 1-100 ml, preferably 2-10 ml, per 1 g of compound [I].

The reaction of compound [I] with halosilane compound and an agent for diazo reaction completes at generally 0-60° C., preferably 20-60° C., for generally 5-20 hr.

When R is acyl group, 2,6-dihalopurine can be obtained by adjusting the pH of the reaction mixture to 2-5, preferably 4-5, after the completion of the reaction. As a method for adjusting the pH of the reaction mixture, for example, a method comprising addition of an aqueous alkali solution (e.g., aqueous sodium hydroxide solution etc.) to the reaction mixture, a method comprising addition of an aqueous alkali solution to the reaction mixture and addition of an aqueous acidic solution (e.g., hydrochloric acid etc.) and the like can be mentioned.

The obtained 2,6-dihalopurine can be isolated and purified by a conventional method. For example, the obtained reaction mixture is cooled, and the precipitated crystals are collected by filtration and dried. The collected crystals are washed or recrystallized to give crystals having a higher purity.

The obtained 2,6-dihalopurine can be converted to a nucleoside analog useful as a pharmaceutical product according to the method described in, for example, EP656,778.

The compound [I] as the starting material can be obtained by the following method.

The compound [I] wherein R is hydrogen atom is commercially available and a commercially available one can be used for the reaction. It is needless to say that one produced by a known method (e.g., EP543,095 etc.) can be used.

The compound [I] wherein R is acyl group can be obtained by, for example, introducing an acyl group into the 7-position or 9-position of compound [I], wherein R is hydrogen atom, according to a conventional method. An acyl group can be generally introduced in the same manner as the protection of amino group with acyl group. For example, compound [I] wherein R is hydrogen atom is reacted with R'—C(=O)OH wherein R' is a hydrocarbon group defined above, or a reactive derivative thereof (e.g., ester, acid halide, acid anhydride etc.) to give compound [I] wherein R is acyl group.

The introduction of acyl group is explained in the following.

When compound [I] wherein R is hydrogen atom is reacted with acid halide, a base is preferably co-used from the aspect of improved reactivity and economical aspect. Examples of the base include organic base (e.g., triethylamine and the like), and inorganic base (e.g., carbonate, hydrogencarbonate and the like). The amount of the base to be used is 1-3 mol, preferably 1.1-2 mol, per 1 mol of compound [I] wherein R is hydrogen atom.

The amount of R'—C(=O)OH and a reactive derivative thereof to be used for introduction of acyl group is generally 1-3 mol, preferably 1.1-2 mol, per 1 mol of compound [I] wherein R is hydrogen atom.

The acyl group can be introduced without a solvent or in an organic solvent, and the introduction without a solvent is economical and convenient because the solvent does not need to be evaporated. When it is introduced in an organic solvent, as the organic solvent, the same solvent as the organic solvent used for the above-mentioned reaction of compound [I] with halosilane compound and an agent for diazo reaction can be used. Other than that, N,N-dimethylacetamide, tetrahydrofuran, ethyl acetate and the like can be used. From the aspect of reactivity, the use of N,N-dimethylacetamide is preferable. The use of the same solvent as the organic solvent used for the above-mentioned reaction of compound [I] with halosilane compound and an agent for diazo reaction is preferable, because the solvent does not need to be evaporated and, after the formation of compound [I], compound [I] can be reacted with halosilane compound and an agent for diazo reaction in one pot without isolation. When the reaction is carried out in an organic solvent, the amount of the organic solvent to be used is 1-20 parts by weight, preferably 2-5 parts by weight, per 1 part by weight of compound [I] wherein R is hydrogen atom.

While the introduction of acyl group varies depending on the reaction conditions and the like, it is completed at generally 1-100° C., preferably 40-60° C., for generally 1 hr-10 hr, preferably 3 hr-6 hr.

EXAMPLES

The present invention is explained in detail in the following by referring to Examples. The present invention is not limited by these examples.

Example 1

(1) Synthesis of 9-acetyl-2-amino-6-chloropurine

2-Amino-6-chloropurine (150 g, 0.89 mol) and acetic anhydride (108 g, 1.06 mol) were added to N,N-dimethylacetamide (350 ml), and the mixture was heated to 50-60° C. and stirred for 4 hr. The reaction mixture was cooled and filtrated. The obtained crystals were washed with isopropanol (400 ml) and dried at 80° C. under reduced pressure to give 9-acetyl-2-amino-6-chloropurine as a pale-yellow powder (187 g, yield 99.0%).

$^1$H-NMR (400 MHz, DMSO-$d_6$) δ=2.83(s,3H), 7.26(brs, 2H), 8.55(s,1H). $^{13}$C-NMR (100 MHz, DMSO-$d_6$) δ=24.65, 124.02, 139.73, 150.09, 152.89, 160.13, 167.69.

(2) Synthesis of 2,6-dichloropurine

9-Acetyl-2-amino-6-chloropurine (0.50 g, 2.36 mmol), dichlorodimethylsilane (1.01 g, 7.80 mmol), tetraethylammonium chloride (0.025 g, 0.15 mmol) and isoamyl nitrite (0.42 g, 3.54 mmol) were added to heptane (4 ml), and the mixture was heated to 50-60° C. and stirred for 14 hr. After the completion of the reaction, the mixture was filtrated. The obtained crystals were diluted with water (4.0 ml), and the mixture was adjusted to pH 4-5 with a 2M aqueous sodium hydroxide solution. After aging under ice-cooling for 1 hr, the mixture was filtered, and the obtained crystals were dried under reduced pressure at 80° C. to give a white powder (0.31 g, yield 73.8%) of 2,6-dichloropurine.

melting point: 184-186° C. $^1$H-NMR(400 MHz, DMSO-d$_6$) δ=8.74(s,1H), 14.15(s,1H). $^{13}$C-NMR(100 MHz, DMSO-d$_6$) δ=128.35, 147.16, 150.58, 155.93.

Example 2

Synthesis of 2,6-dichloropurine

9-Acetyl-2-amino-6-chloropurine (0.50 g, 2.36 mmol), tetraethylammonium chloride (0.025 g, 0.15 mmol) and isoamyl nitrite (0.42 g, 3.54 mmol) were added to chlorotrimethylsilane (4.0 g, 36.8 mmol), and the mixture was heated to 50-60° C. and stirred for 10 hr. After the completion of the reaction, the mixture was filtered. The obtained crystals were diluted with water (4.0 ml), and the mixture was adjusted to pH 4-5 with a 2M aqueous sodium hydroxide solution. After aging under ice-cooling for 1 hr, the mixture was filtered, and the obtained crystals were dried under reduced pressure at 80° C. to give 2,6-dichloropurine as a white powder (0.35 g, yield 78.3%). The properties of the obtained compound were the same as in Example 1(2).

Example 3

Synthesis of 2,6-dichloropurine

9-Acetyl-2-amino-6-chloropurine (2.50 g, 11.8 mmol), dichlorodimethylsilane (4.57 g, 35.4 mmol), benzyltriethylammonium chloride (0.16 g, 0.70 mmol) and isoamyl nitrite (2.07 g, 17.7 mmol) were added to o-dichlorobenzene (10 ml), and the mixture was heated to 25-30° C. and stirred for 8 hr. After the completion of the reaction, the mixture was filtered. The obtained crystals were diluted with water (4.0 ml), and the reaction mixture was added dropwise to 2M aqueous sodium hydroxide solution (20 ml) and partitioned. The aqueous layer was adjusted to pH 4-5 with 35% hydrochloric acid. After aging under ice-cooling for 1 hr, the mixture was filtered, and the obtained crystals were dried under reduced pressure at 80° C. to give 2,6-dichloropurine as a white powder (1.62 g, yield 72.6%). The properties of the obtained compound were the same as in Example 1(2).

Example 4

Synthesis of 2,6-dichloropurine

2-Amino-6-chloropurine (5.00 g, 29.5 mmol), dichlorodimethylsilane (11.42 g, 88.5 mmol), benzyltriethylammonium chloride (0.40 g, 1.8 mmol) and isoamyl nitrite (5.18 g, 44.2 mmol) were added to heptane (25 ml), and the mixture was heated to 50-60° C. and stirred for 17 hr. After the completion of the reaction, the mixture was filtered. The obtained crystals were diluted with water (25 ml) and adjusted to pH 4-5 with a 2M aqueous sodium hydroxide solution. After aging under ice-cooling for 1 hr, the mixture was filtered, and the obtained crystals were recrystallized from methanol. The mixture was dried under reduced pressure at 60° C. to give 2,6-dichloropurine as a white powder (3.68 g, yield 66.1%). The properties of the obtained compound were the same as in Example 1(2).

Example 5

(1) Synthesis of 9-acetyl-2-amino-6-iodopurine

In the same manner as in Example 1 except that 2-amino-6-iodopurine was used instead of 2-amino-6-chloropurine, the mixture was stirred for 15 hr. The reaction mixture was subjected to post-treatment in the same manner as in Example 1 to give 9-acetyl-2-amino-6-iodopurine as a white powder.

(yield 94.6%) $^1$H-NMR(400 MHz, DMSO-d$_6$) δ=2.82(s, 3H), 7.18(brs,2H), 8.51(s,1H) $^{13}$C-NMR(100 MHz, DMSO-d$_6$) δ=24.80, 124.02, 131.04, 138.82, 149.02, 159.88, 167.90

(2) Synthesis of 2-bromo-6-iodopurine

9-Acetyl-2-amino-6-iodopurine (1.44 g, 4.72 mmol), bromotrimethylsilane (2.17 g, 14.2 mmol) and isoamyl nitrite (0.83 g, 5.67 mmol) were added to tetrahydrofuran (5 ml), and the mixture was stirred 20-25° C. for 19 hr to give 2-bromo-6-iodopurine.

LC/MS(−c ESI) m/z 323, 325(M$^{−1}$)

Example 6

Synthesis of 2-bromo-6-chloropurine

9-Acetyl-2-amino-6-chloropurine (1.00 g, 4.72 mmol), bromotrimethylsilane (2.17 g, 14.2 mmol) and isoamyl nitrite (0.83 g, 5.67 mmol) were added to tetrahydrofuran (5 ml), and the mixture was stirred at 20-25° C. for 19 hr to give 2-bromo-6-chloropurine.

LC/MS(−c ESI) m/z 231, 233, 235 (M$^{−1}$)

INDUSTRIAL APPLICABILITY

According to the present invention, the objective 2,6-dihalopurine can be produced conveniently in a high yield and easily isolated.

This application is based on patent application No. 2002-102456 filed in Japan, the contents of which are hereby incorporated by reference.

What is claimed is:

1. A production method of 2,6-dihalopurine of the formula [II]

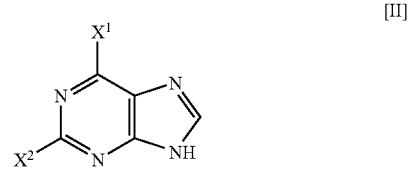

wherein $X^1$ and $X^2$ are the same or different and each is a halogen atom, which comprises reacting a compound of the formula [Ia] [Ib]

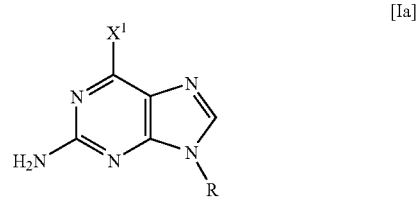

-continued

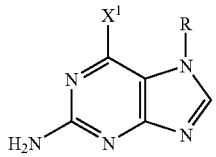
[Ib]

wherein X¹ is a halogen atom and R is a hydrogen atom or acyl group, with a halosilane compound and an agent for diazo reaction in the presence of a quarternary ammonium salt.

2. The production method of claim 1, wherein the quarternary ammonium salt is tetraethylammonium chloride or benzyltriethylammonium chloride.

3. A production method of 2,6-dihalopurine of the formula [II]

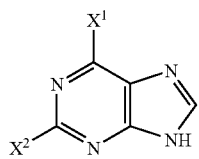
[II]

wherein X¹ and X² are the same or different and each is a halogen atom, which comprises reacting a compound of the formula [Ia] or [Ib]

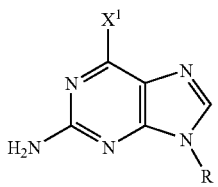
[Ia]

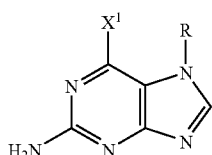
[Ib]

wherein X¹ is a halogen atom and R is an acyl group, with a halosilane compound and an agent for diazo reaction.

4. The production method of claim 3, wherein the acyl group for R is acetyl group.

5. A production method of 2,6-dihalopurine of the formula [II]

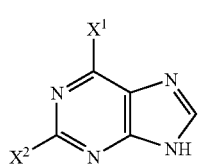
[II]

wherein X¹ and X² are the same or different and each is a halogen atom, which comprises reacting a compound of the formula [Ia] or [Ib]

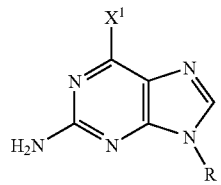
[Ia]

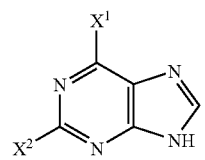
[Ib]

wherein X¹ is a halogen atom and R is a acyl group, with a halosilane compound and an agent for diazo reaction, wherein the halosilane compound is chlorotrimethylsilane or dichlorodimethylsilane.

6. A production method of 2,6-dihalopurine of the formula [II]

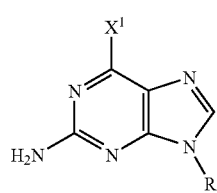
[II]

wherein X¹ and X² are the same or different and each is a halogen atom, which comprises reacting a compound of the formula [Ia] or [Ib]

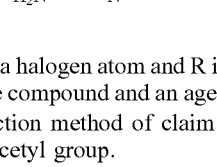
[Ia]

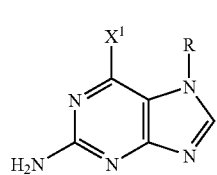
[Ib]

wherein X¹ is a halogen atom and R is a hydrogen atom or acyl group, with a halosilane compound and an agent for diazo reaction, wherein, after introducing an acyl group into the 9-position or the 7-position of compound of the formula [Ia] or [Ib], wherein R is a hydrogen atom, the obtained compound of the formula [Ia] or [Ib], wherein R is acyl group, is reacted with halosilane compound and the agent for diazo reaction.

* * * * *